United States Patent [19] … [11] Patent Number: 5,051,249
Metcoff … [45] Date of Patent: * Sep. 24, 1991

[54] METHOD OF NUTRITIONAL THERAPY

[76] Inventor: Jack Metcoff, 103 Lake Aluma Dr., Oklahoma City, Okla. 73121

[*] Notice: The portion of the term of this patent subsequent to Apr. 4, 2006 has been disclaimed.

[21] Appl. No.: 463,589

[22] Filed: Jan. 11, 1990

[51] Int. Cl.$^5$ .................... A61K 49/00; A61K 31/40; A61K 31/195

[52] U.S. Cl. ....................................... 424/9; 514/419; 514/561

[58] Field of Search ...................... 424/9; 514/561, 419

[56] References Cited

U.S. PATENT DOCUMENTS

| | | | |
|---|---|---|---|
| 3,649,269 | 3/1972 | Kubota | 430/23 |
| 3,778,615 | 12/1973 | Luckey | 430/6 |
| 4,273,842 | 6/1981 | Nonogaki | 430/144 |
| 4,279,917 | 7/1981 | Takami et al. | 424/273 R |
| 4,612,268 | 9/1986 | Miura | 430/23 |
| 4,748,102 | 5/1988 | Weller, Jr. | 430/258 |
| 4,818,516 | 4/1989 | Metcoff | 424/9 |
| 4,920,030 | 4/1990 | Ichimura | 430/287 |

OTHER PUBLICATIONS

Beck et al., "The Aerobic Carbohydrate Metabolism of Leukocytes in Health and Leukemia I. Glycolysis and Respiration", Cancer Res., 12:818-822 (1952).
Beck et al., "The Aerobic Carbohydrate Metabolism of Leukocytes in Health and Leukemia II. The Effect of Various Substrates and Coenzymes on Glycolysis and Coenzymes on Glycolysis and Respiration", Cancer Res., 12:823-828 (1952).
Bucher et al., "Pyruvate Kinase from Muscle", Methods in Enzymology, Colowick et al., Eds., Academic Press Inc., N.Y., 1:435-440 (1955).
Horecker et al., "Glucose-6-Phosphate Dehydrogenase", Methods in Enzymology, Colowick et al., Eds., Academic Press Inc., N.Y., 1:323-327 (1955).
Beck, "The Control of Leukocyte Glycolysis", J. Biol. Chem., 232:251-270 (1958).
Beck, "Occurrence and Control of the Phosphogluconate Oxidation Pathway in Normal and Leukemic Leukocytes", J. Biol. Chem., 232:271-283 (1958).
Noble et al., "Carbohydrate Metabolism in the Leukocytes I. The Pathway of Two- and Three-Carbon Compounds in the Rabbit Polymorphonuclear Leukocyte", J. Biol. Chem., 235:1261-1264 (1960).
Vannotti, "Metabolic Pattern of Leukocytes Within the Circulation Outside It", Biol. Activity of the Leukocyte, Ciba Fndtn. Study Grp. #10, Boston, Mass., Little Brown Pub., 79-85 (1961).
Frei et al., "Enzymatic Studies in the Different Types of Normal and Leukemic Human White Cells", Blood, 18:317-327 (1961).
Rosenberg et al., "Transport of Neutral and Dibasic Amino Acids by Human Leukocytes: Absence of Defect in Cystinuria", J. Clin. Inv., 44:1382-1393 (1965).

Weber et al., "Insulin: Inducer of Pyruvate Kinase", Science, 149:65-67 (1965).
Giles et al., "An Improved Diphenylamine Method for the Estimation of Deoxyribonucleic Acid", Nature, 206:93 (1965).
Campos et al., "Kinetic Differences Between Human Red Cell and Leukocyte Pyruvate Kinase", Nature, 208:194-195 (1965).
Krebs et al., "The Role of Pyruvate Kinase in the Regulation of Gluconeogenesis", Biochem. J., 94:3c-4c (1965).
Selvaraj et al., "Relationship of Glycolytic and Oxidative Metabolism to Particle Entry and Destruction in Phagocytosin Cells", Nature, 211:1272-1276 (1966).
Yoshida et al., "Intermediary Metabolites and Adenine Nucleotides in Leukocytes of Children with Protein-Calorie Malnutrition", Nature, 214:525-526 (1967).
Minakami, "Studies on Leukocyte Metabolism I. Glycolytic Intermediates and Nucleotides in Guinea Pig Exudate Granulocytes", J. Biochem., 63:83-88 (1968).
Rhoads et al., "Initial Velocity and Equilibrium Kinetics of Myokinase", J. Biol. Chem., 243:3963-3972 (1968).
Boyum, "Isolation of Leukocytes from Human Blood Further Observations", Scand. J. Clin. Lab. Invest., 21:31-50 (1968).
Boyum, "A One-Stage Procedure for Isolation of Granulocytes and Lymphocytes from Human Blood", Scand., J. Clin. Lab. Invest., 21:51-76 (1968).
Leung et al., "Effect of Amino Acid Imbalance on Plasma and Tissue Free Amino Acids in the Rat", J. Nutr., 96:303-318 (1968).
Baierlein et al., "Studies on the Energy Metabolism of Human Leukocytes II. Mechanism of the Pasteur Effect in Human Leukocytes", Blood, 32:412-422 (1968).

(List continued on next page.)

Primary Examiner—Frederick E. Waddell
Assistant Examiner—Raymond J. Henley, III
Attorney, Agent, or Firm—Mary M. Lee

[57] ABSTRACT

A method for treating a nutritional disorder in a subject. The subject's nutritional status first is assessed by measuring a selected intracellular metabolic process. Upon determination that the metabolic process is not functioning normally, a set of intracellular or "primary" nutrients are identified for the metabolic process. The level of each primary nutrient is compared to normal. A set of extracellular or "secondary" nutrients is identified for each of the subject's abnormal primary nutrients. The normal values for the metabolic processes, the identification of normal primary nutrients and the set of secondary nutrients for each primary nutrient are determined by studying a population of normal subjects analogous to the subject in need of treatment. Treatment of the subject includes administration of a composition comprising a calculated concentration of the second nutrients identified for each of the subject's abnormal primary nutrients.

7 Claims, No Drawings

OTHER PUBLICATIONS

Yoshida et al., "Reduced Pyruvic Kinase Activity, Altred Growth Patterns of ATP in Leukocytes, and Protein-Calorie Malnutrition", Am. J. Clin. Nutr., 21:162–166 (1968).

Atkinson, "The Energy Charge of the Adenylate Pool as a Regulatory Parameter. Interaction with Feedback Modifiers", Biochem., 7:4030–4034 (1968).

Gallo et al., "The Enzymatic Mechanism for Deoxythymidine Synthesis in Human Leukocytes IV. Comparisons Between Normal and Leukemic Leukocytes", J. Clin. Invest., 48:105–116 (1969).

Baron et al., "Intracellular Concentrations of Water and of the Principal Electrolytes Determined by Analysis of Isolated Human Leukocytes", Clin. Sci., 37:205–219 (1969).

Brenner et al., "Control of Aminoacyl Transfer Ribonucleic Acid Synthetases", J. Biol. Chem., 245:450–452 (1970).

Baehner et al., "Respiration and Glucose Oxidation in Human and Guinea Pig Leukocytes: Comparative Studies", J. Clin. Invest., 49:692–700 (1970).

Metcoff et al., "Biomolecular Studies of Fetal Malnutrition in Maternal Leukocytes", Pediatrics, 47:180–191 (1971).

Jemelin et al., "Metabolisme Energetique du Leukocyte", Ann. Biol. Clin., 29:109–111 (1971).

Winkler et al., "Proteinsynthese in Menschlichen Leukocytes", Klin. Wschr., 49:225–227 (1971).

Yoshida et al., "Human Fetal Growth Retardation: II. Energy Metabolism in Leukocytes", Pediatrics, 50:559–567 (1972).

Winkler, "Kinetics of the Flow of Amino Acids from the Extracellular Space and the Intracellular Pools Resulting in Protein Synthesis", Hoppe-Seyler's Z. Physiol. Chem., 353:782–786 (1972).

Winkler et al., "Protein Synthesis in Human Leukocytes, IV. Mutual Inhibition of Amino Acid Incorporation by Amino Acids in Cell-Free Systems", Hoppe-Seyler's Z. Physiol. Chem., 353:787–792 (1972).

Van Berkel et al., "M-Type Pyruvate Kinase of Leukocytes: an Allosteric Enzyme", Biochem. Biophys. Acta, 293:134–139 (1973).

Metcoff et al., "Energy Metabolism and Protein Synthesis in Human Leukocytes During Pregnancy and in Placenta Related to Fetal Growth", Pediatrics, 51:866–877 (1973).

Patrick et al., "The Response of the Human Leukocyte to Alterations in Extracellular Osmolality", Clin. Sci., 44:457–465 (1973).

Hilton et al., "Sodium and Potassium Flux Rates in Normal Human Leukocytes in an Artificial Extracellular Fluid", Clin. Sci., 44:439–445 (1973).

DeChatelet et al., "Inhibition of Amino Acid Incorporation into Protein of Human Neutrophils by Phagocytosis", Infection & Immun., 8:791–795 (1973).

Van Berkel, "Some Kinetic Properties of $M_2$-Type Pyruvate Kinase from Rat Liver at Physiological $Mg^{2+}$ Concentration", Biochimica et Biophys. Acta, 37:140–152 (1974).

Metcoff, "Biochemical Markers of Intrauterine Malnutrition", Nutrition and Fetal Development, Winick, Ed., J. Wiley & Sons, Pub., pp. 27–44 (1974).

Metcoff, "Enzymatic Indices of Fetal Malnutrition", Mod. Prob. Pediat., Falkner et al., Eds., S. Karger, Pub., 14:57–67 (1975).

Metcoff, "Cellular Energy Metabolism in Protein-Calorie Malnutrition", In Protein-Calorie Malnutri., Academic Press, pp. 65–85 (1975).

Mameesh et al., "Kinetic Properties of Pyruvate Kinase in Human Maternal Leukocytes in Fetal Malnutrition", Ped. Res., 10:561–565 (1976).

Houpert et al., "Comparison of Procedures for Extracting Free Amino Acids from Polymorphonuclear Leukocytes", Clin. Chem., 22:1618–1622 (1976).

Shinnick et al., "Effects of Branched-Chain Amino Acid Antagonism in the Rat on Tissue Amino Acid and Keto Acid Concentrations", J. Nutr., 107:887–895 (1977).

Metcoff, "Relationship of Leukocyte Metabolism to Maternal Nutritional Status and Fetal Growth", In: Malnutrition and the Immune Response, R. Suskind, Ed., Raven Press, N.Y., pp. 285–292 (1977).

"Leukocyte Transketolase Activity: An Indicator of Thiamin Nutriture", Nutr. Reviews, 35:185–187 (1977).

Crosby et al., "Fetal Malnutrition: an Appraisal of Correlated Factors": Am. J. Obst. & Gynec., 128:22–31 (1977).

Patrick et al., "Leukocyte Electrolytes and Sodium Transport in Protein Energy Malnutrition", Am. J. Clin. Nutr., 30:1478–1481 (1977).

McClain et al., "Relationship of Maternal Amino Acid Profiles at 25 Weeks of Gestation to Fetal Growth", Am. J. Clin. Nutr., 31:401–407 (1978).

Metcoff et al., "Cell Metabolism in Uremia", Am. J. Clin. Nutr., 31:1627–1634 (1978).

Baron et al., "Intracellular Chemical Pathology", In: Recent Adv. in Clin. Biochem., Churchill, Livingston, N.Y., 1:153–174 (1978).

Ghisolfi et al., "Plasma Free Amino Acids in Normal Children and in Patients with Proteinocaloric Malnutrition: Fasting and Infections", Ped. Res., 12:912–917 (1978).

Tews et al., "Induction of Threonine Imbalance by Dispensable Amino Acids: Relation to Competition for Amino Acid Transport into Brain", 109:304–315 (1978).

Wells et al., "Leukocyte Amino Acid Concentrations and Their Relationship to Changes in Plasma Amino Acids", J. Parent. & Ent. Nutr., 4:264–267 (1980).

Metcoff, "Maternal Nutrition and Fetal Development", In: Early Human Development, 4:99–120, Elsevier/North-Holland Biomedical Press (1980).

Metcoff et al., "Material Nutrition and Fetal Outcome", Am. J. Clin. Nutr., 34:708–721 (1981).

Rannels et al., "The Measurement of Protein Synthesis in Biological Systems", Life Sciences, 30:1679–1690 (1982).

Fukuda et al., "Characteristic Patterns of Free Amino Acid Content in Plasma, Erythrocytes, Lymphocytes and Granulocytes in Man", Kiroshima J. Med. Sci., 32:163–166 (1983).

(List continued on next page.)

OTHER PUBLICATIONS

Metcoff et al., "Effects of Amino Acid Infusions on Cell Metabolism in Hemodialyzed Patients with Uremia", Kidney Internat., 24:S-87-S-92 (1983).

Patrick et al., 37 Leukocyte Zinc in the Assessment of Zinc Status", CRC Crit. Rev. Clin. Lab. Sci., 20:95-114 (1984).

Metcoff et al., "Effect of Food Supplementation (WIC) During Pregnancy on Birth Weight", Am. J. Clin. Nutr., 41:933-947 (May, 1985).

Metcoff et al., "Cellular Abnormalities in Uremia", CAPD in Children, Fine et al., eds., Springer-Verlag Heidelberg, pp. 1-13 (1985).

Johnson et al., "Relation of Protein Synthesis to Plasma and Cell Amino Acids in Neonates", Ped. Res., 20:2, 140-146 (1986).

Metcoff, "Malnutrition at the Cellular Level in Uremia: A New Frontier for Research", J. Am. Coll. Nutr., 5:229-241 (1986).

Metcoff, "Intracellular Amino Acid Levels as Predictors of Protein Synthesis", J. Am. Coll. Nutr., 5:107-120 (1986).

Metcoff, "Cell Metabolism in Uremia", In: Recent Adv. in Ped. Nephr., K. Murakami et al., eds., Elsevier Science/Biomed. Div. pub., pp. 215-222 (1987).

Metcoff et al., "Protein Synthesis, Cellulor Amino Acids, and Energy Levels in CAPD Patients", Kidney Int'l., 32:Supp. 22, S-136-S-144 (1987).

Metcoff, "Effect of CAPD vs. Hemodialysis on Protein Synthesis in Uremic Patients, In Nieren-und Hochdruckkrankheiten, 17:Supp.1, S.10-16 (1988).

Metcoff et al., "Relation of Amino Acids, Energy Levels and Protein Synthesis in Chronic Renal Disease", Child Nephr. Urol., 9:153-159 (1988-89).

Metcoff et al., "Nutritional Problems of Children with Chronic Renal Failure", Nutr. in Clin. Prac., pp. 172-191 (1989).

Metcoff et al., "Energy Production, Intracellular Amino Acid Pools, and Protein Synthesis in Chronic Renal Disease", J. Am. Coll. Nutr., 8:4, 271-284 (1989).

METHOD OF NUTRITIONAL THERAPY

This invention was made with government support. The government has certain rights in this invention.

The subject matter of this application is related to the subject matter of U.S. Pat. No. 4,818,516, issued Apr. 4, 1989.

FIELD OF THE INVENTION

The present invention relates generally to methods of treating nutritional disorders in subjects.

SUMMARY OF THE INVENTION

The present invention is directed to a method for treating a subject for a nutritional disorder. The rate of a selected intracellular metabolic process is measured. A set of primary (intracellular) nutrients is identified for the metabolic process. The identification is based on a multivariate statistical analysis of intracellular nutrients in a population of normal study subjects analogous to the subject to be treated in accordance with this invention. The subject's primary nutrients are measured and it is determined, based on normal levels identified for the study population, which primary nutrients are present at abnormal levels.

For each of the primary nutrients present at an abnormal level, a set of secondary (extracellular) nutrients is identified. The set of secondary nutrients is selected based on the normal set of secondary nutrients in the study population determined by multivariate statistical analysis for each of the primary nutrients in the study population, producing for each secondary nutrient a partial regression coefficient having a positive or negative sign.

Then an effective amount of a nutrient composition is administered to the subject. The composition comprises each of the secondary nutrients in a concentration selected according to the following formula:

$$[F] = A[B] + [B]$$

where "[F]" is the final concentration in nanomoles per milliliter of the secondary nutrient in the nutrient composition; where A equals the partial regression coefficient of the secondary nutrient, including sign, divided by the sum of the coefficients, disregarding their signs, of all the secondary nutrients, such sum being expressed as a positive number; and where "[B]" is the normal concentration of the secondary amino acid in the study population expressed in nanomoles per milliliter.

DESCRIPTION OF THE PREFERRED EMBODIMENT

Nutritional status is a function of intracellular metabolic processes which synthesize proteins, fats and carbohydrates and generate energy from nutrients which enter the cell from the surrounding body fluids and tissues. These continuous and dynamic metabolic processes are mediated by various enzyme systems. If the enzyme systems are intact, the success of the metabolic processes depend on the quality, quantity and balance within the cell of the nutrients, such as amino acids, electrolytes, trace minerals and glucose.

The diagnosis and treatment of nutritional disorders, such as malnutrition and Kwashiorkor, traditionally have been based primarily on visual examination and fat fold and upper arm circumference measurements. Plasma levels of nutrients also have been analyzed. Other types of moderate to severe malnutrition have been treated by intravenous solutions comprising a broad spectrum of nutrients with emphasis on protein and calories, a so called "shot gun" approach. When intravenous treatment is needed, a nutrient solution comprising standard concentrations of amino acid salts, vitamins, etc. is used.

The present invention is directed to a method for accurately assessing the nutritional status of a subject by measurement of intracellular nutrient levels and analysis of metabolic processes. Based on data obtained from a population of study subjects, a subset of intracellular nutrients which normally accounts for a relatively large and significant proportion of the variance in the selected nutrient-dependent metabolic process, such as protein synthesis, is identified. The nutrients which make up this subset are referred to herein as primary nutrients.

Likewise, by analyzing concurrent plasma levels of nutrients in conjunction with such intracellular measurements in a population of study subjects, a subset of extracellular nutrients may be identified which normally are not correlated with, but account for, levels of primary nutrients within the cells. Thus, these plasma nutrients, called secondary nutrients, indirectly improve the function of the intracellular metabolic processes. By administering to the subject having a nutritional disorder, depleting primary nutrients, a nutrient composition comprising a combination of secondary nutrients in concentrations calculated to correct the subject's abnormal intracellular levels of primary nutrients, the nutritional disorder may be treated.

As metabolic processes occur in all nucleated cells, nucleated cells from any body tissue are suitable for measuring intracellular nutrients and metabolic activities. Leukocytes are preferred cells for these measurements as leukocytes are readily accessible, have relatively short half-lives in circulation, are rapidly reproduced, and have a high rate of protein synthesis in relation to protein degradation.

The procedures described below are adapted for leukocytes. It is to be understood that where cells of other body tissues are selected to be measured, the procedures should be modified accordingly. For example, where muscle cells are selected, such cells may be obtained by needle biopsy instead of venous blood sampling which is the preferred method for obtaining blood cells, such as leukocytes.

Obtaining a Cell Sample

To measure nutrient levels and metabolic activity, whether in the subject in need of treatment or in subjects comprising a study population, suitable cells are obtained. As stated, leukocytes are preferred. Where leukocytes are selected, a venous blood sample is obtained, and placed in a vessel in combination with a heparin dextran preparation ("hep-dex"). The amount of the blood sample preferably is about 2.5 ml to 3 ml for infants and 10 ml to 15 ml for older children and adults. The blood sample is withdrawn by venipuncture using a heparinized syringe and then transferred to the vessel. If such a procedure is followed, the needle preferably is removed from the syringe before the blood is expressed into the vessel, and the amount of blood in the syringe is recorded. A preferred vessel is a prechilled, 15 ml plastic conical centrifuge tube.

The hep-dex solution preferably comprises about one million units of sodium heparin (Sigma, No. H3123), about 15 grams of dextran having an average molecular weight of 81,600 (Sigma, D4751), and about 1.27 grams of sodium chloride, in sterile water in an amount sufficient to bring the total volume of solution equal to 250 ml. The solution, which is preferably placed in the vessel before the blood, is combined with the blood in a ratio of about 1 ml of hep-dex solution to about 8 ml of blood.

Having placed the hep-dex solution and the blood sample in the vessel, the vessel is then covered, such as by sealing with a parafilm cap. The contents of the vessel are then gently mixed, such as by manually inverting the vessel about three times. The total volume of fluid in the vessel (the blood from the syringe and the hep-dex solution) is estimated and recorded.

The vessel then preferably is maintained at 4° C. for thirty minutes to allow the blood/hep-dex mixture to settle. For example, the vessel, such as the tube, may be immersed in a larger vessel, such as a beaker, containing crushed ice. In order to facilitate settling and to maximize the surface of the plasma-cel interface, the vessel preferably is tilted at about a 45° angle while settling and preferably is immersed to a depth so that the level of the ice is above the meniscus of the mixture in the tilted vessel.

Separation of Plasma and Granulocytes

After the blood/hep-dex mixture has settled, the plasma and the leukocytes are each separated for testing. The separation procedures described herein are carried out under cold ambient temperatures (4° C.). A centrifugation is used for separation, the plasma first is gently removed from the vessel by non-wettable plastic or siliconized glass pipettes, and then carefully layered over a gradient medium in a centrifuge tube. A preferred centrifuge tube is a 10 ml siliconized glass tube (Vacutainer No. 6430). A preferred gradient medium is a Ficoll solution which is a mixture of Ficoll 400 (a polysaccharide) and sodium diatrizoate, adjusted to a density of 1.077. Suitable Ficoll solutions include Ficoll-Hypaque (Pharmacia) and Sigma No. 1077. In transferring the plasma to the centrifuge tube, great care should be exercised not to allow the plasma to break the interface between the plasma being added and the Ficoll solution, so as to keep the cells which are contained within the plasma, above the Ficoll solution.

The centrifuge tubes containing the plasma and Ficoll solution preferably are gently centrifuged in the cold (4° C.) until the cell layers are well defined. Centrifuging for about 25 minutes at about 250 × g is preferred. It is to be understood that unbalanced centrifuging may cause the cell bands to scatter and be undefined.

After centrifugation, the components of the blood/hepdex mixture will be disposed in well-defined layers as follows: plasma (uppermost in the tube); a white layer comprising lymphocytes; a clear layer comprising Ficoll solution; and granulocytes and erythrocytes pelleted at the bottom of the tube. Each of these layers, except the granulocyte/erythrocyte pellet, is removed one at a time and working from top to bottom, preferably by using a plastic or siliconized pipette (Pasteur).

The plasma preferably is transferred to a vessel, such as a blood collection tube, which tube is kept cool (4° C.), such as by placing it in crushed ice. The Ficoll solution and the lymphocytes may be discarded.

The granulocytes next are isolated by lysing and removing the erythrocytes. The erythrocytes and granulocytes pelleted at the bottom of the tube preferably are resuspended in about 2 ml to about 3 ml of a salt solution comprising isotonic combinations of potassium chloride, and sodium chloride in water. A preferred salt solution is calcium free Hank's Balanced Salt Solution having a pH of about 7.4 and comprising reagent grade water.

The suspension of erythrocytes and granulocytes may then be transferred using a plastic or siliconized pipette (Pasteur) to a conical centrifuge tube which preferably is larger than the tube used to centrifuge the entire sample as described above. A preferred centrifuge tube for the erythrocyte/granulocyte suspension is a 50 ml polypropylene centrifuge tube (Nalgene No. 3103). To assure that substantially all the erythrocytes and granulocytes have been removed from the small tube, another 2 ml to 3 ml salt solution, such as Hank's solution, may be used to rinse the tube and then transferred to the larger conical centrifuge tube.

Additional salt solution, such as Hank's solution, is placed in the conical centrifuge tube to bring the total volume to about 15 ml. The 15 ml mixture should be visually inspected for fibrin clumps. If any are observed, these preferably are removed by aspiration with a siliconized pipette, if possible. The cells in the salt solution preferably are gently centrifuged with balance for about 5 minutes at about 250 × g. The supernatant then is removed by decanting.

The granulocytes and erythrocytes remaining in the tube after removal of the supernatant are resuspended in a solution comprising about 5 ml of a salt solution, as described above, such as Hank's solution, and about 15 ml of distilled water to lyse the erythrocytes. This suspension then is mixed gently at lowest speed on Vortex for exactly thirty seconds. After the thirty second mixing, the solution is immediately returned to isotonicity by adding about 5 ml of 3.5 percent sodium chloride solution. The isotonic suspension then is gently mixed again, and centrifuged again with balance for about 5 minutes at about 250 × g. The supernatant then is removed, as by decanting, and discarded.

The pellet of cells remaining after the lysis procedure, comprising substantially all granulocytes, preferably is washed again. The cells may be resuspended in about 15 ml of isotonic salt solution, such as Hank's solution, and gently centrifuged with balance at about 250 × g for about 5 minutes. The supernatant is removed, such as by decanting it out of the tube. The pellet of cells will remain adhered to the bottom of the centrifuge tube. The centrifuge tube is inverted and allowed to drain for about one minute.

The pellet of cells next preferably is resuspended in about 0.5 ml of 0.16M potassium chloride. This suspension o granulocytes is in condition for dilution and analysis. It should be noted that the separation and preparation of granulocytes should 10 be completed within about two hours from the time the venous blood sample was obtained from the patient. At all times the cells must be handled gently and should be maintained under cool conditions, preferably at 4° C., such as on ice or in a cold (4° C.) room, to maintain cell viability.

The percentage of the granulocytes may be counted automatically, as by a Coulter counter, or manually by direct microscopic visualization of a hemocytometer containing the appropriate dilution of cells. To determine whether the cells are viable, about 1 drop (50 μl)

of a vital dye, preferably Trypan blue 0.05%, is added to the suspension on the hemocytometer. One hundred cells are counted. The viable cells do not allow the dye to enter. Cells which are not viable take up the dye. When the isolation procedure is satisfactory, about 95% to 97% of the granulocytes will be viable and will exclude the dye.

Dilution of Granulocyte Preparation

The preparation of concentrated granulocytes preferably is diluted in 0.16M potassium chloride to a concentration which is suitable for analysis. The concentration is measured by optical density. An absorbance of 340 nm preferably is used as a reference. A preferred final solution reads about 0.30 to about 0.50, at $A_{340}$ of a 1:21 dilution.

The concentrated granulocyte suspension preferably is diluted by adding small amounts of the potassium chloride solution in increments until the desired concentration is obtained. For example, about 10 μl of the concentrated granulocyte suspension may be added to a vessel, such as a cuvette containing about 200 μl of the potassium chloride solution. The mixture may then be stirred with a plastic stirring stick and the optical density measured.

If the optical density indicates that the mixture is still too concentrated, additional potassium chloride solution may be added and the optical density measured again.

As regards optical density measurement, it is preferable to take each measurement at least twice. A third reading should be taken if the first two readings differ by more than five percent. In any event, each optical density measurement should be recorded.

It should be noted that the granulocytes settle out of suspension relatively rapidly. For this reason, the concentrated granulocyte suspension should be gently agitated to remix the suspension prior to taking any sample or aliquot from it. At all times the suspensions of granulocytes, diluted and concentrated, should be handled gently and kept at about 4° C. (on ice) whenever possible.

Measurement of Intracellular and Extracellular Water

The intracellular and extracellular water content of the isolated granulocytes preferably is measured. A measured volume, preferably less than 0.1 ml, of the diluted granulocyte suspension, prepared as described above, preferably is placed in a clean, dry and preweighed microcentrifuge tube, such as a 1 ml polyethylene microcentrifuge tube (Fisher No. 05-407-5). The granulocytes are packed, preferably by gentle centrifugation for about 5 minutes at about 200 × g. The supernatant is then removed and the microcentrifuge tube is turned upside down and allowed to drain on filter paper for about one minute.

To obtain an accurate weight of the granulocytes, excess moisture preferably is removed from the microcentrifuge tube such as by using a lint-free wiper to wipe the inside of the tube. The tube containing the granulocyte is then weighed, preferably on a microanalytical balance readable to 0.01 mg (Mettler), to obtain a "wet" weight. To ensure an accurate weight the tube should be handled using dry, plastic gloves or forceps. The granulocytes are then resuspended, preferably in a tris-citrate solution, such as 0.1M tris-citrate, pH 7., in a volume equal to the measured amount, less 10 μl of diluted granulocyte suspension placed in the microcentrifuge tube prior to obtaining the wet weight.

Radio isotope-labeled inulin, about 10 μl, is added to the granulocyte-tris-citrate solution which is mixed gently. A suitable inulin for this purpose is $^{14}C$ inulin at a concentration of 11 mg/ml in 0.1M tris-citrate, pH 7.4, so that it contains 0.25 μCi/10 μl. The mixture is centrifuged gently at about 200 × g for about 5 minutes. The supernatant is removed and the tube weighed as before.

Next the granulocyte pellet is freed, as by adding a small amount of the tris solution. The free granulocytes are then transferred to a pre-weighed paper filter, such as a Whatman GF/A 2.4 cm filter. The filter containing the granulocytes is transferred, preferably using forceps, to an oven having an adjustable temperature for drying. The filter is heated in the oven for about one to about two hours at about 75° C. Again using forceps, the filter with the dried cells is cooled to ambient temperature in a desiccator, weighed on a balance as before and the dry weight recorded.

A second 2.4 Whatman paper filter is preweighed, and an amount of tris solution equal to that used to dilute and also free the granulocyte pellet is placed on the filter paper. This is used as a control "blank". The filter is weighed for a wet weight and then dried in the oven at the same time as the filter containing the granulocytes. The wet weight of the blank filter minus its dry weight represents the weight of the tris salts contained in the solution used to dilute and then "free" the granulocyte pellet. This value is subtracted from the dry weight of the filter containing the dried granulocyte suspension, which includes the dried tris salt. The resultant value is the true dry weight of the granulocytes.

After the dry weight is measured, the dried filter containing the cells is placed in a scintillation vial. A scintillator fluid "cocktail" comprising 0.4% PPO (2.5-diphenyloxazole) 0.01% POPOP (1.4 bis [2-(5-phenyloxazolyl)] benzene) in toluene, in weight for volume of toluene, is next added to the vial and placed in a scintillation counter and counted three times at five minute intervals in the dissociations per minute (DPM) mode.

It should be noted that it is necessary to know the number of DPM's added to the 10 μl suspension containing the labeled inulin solution. This may be determined for a single batch separately by pipetting 10 μl of the $^{14}C$ inulin solution directly onto a filter, drying and counting as above. The known value of the activity of a single batch may then be used in subsequent scintillation counts using the same labeled inulin solution.

The extracellular water content may be calculated using the following equations:

Wet weight($A$) = Wt. of tube + cells − Wt. of tube.

Dry weight($B$) = Wt. of filter + dried cells − Wt. of filter.

Water weight($C$) = A − B.

$$\text{Extracellular water}(ECW) = \frac{\text{DPMs of dried cells}}{\text{DPMs}/10\ \mu l} \times C.$$

Intracellular water (ICW) = C − ECW.

$$\text{Percent of } ICW = \frac{ICW}{A - ECW} \times 100.$$

The theory of using radioactive inulin to calculate ECW is based on the observation that inulin, a high molecular weight starch, is not metabolized, and does not bind to, or cross, the cell membrane, but instead remains in the extracellular fluid, not otherwise affecting cell structure or viability. As the cells are pelleted by centrifugation, a certain amount of the suspending solution is trapped between the cells. Using higher g's to pack the cells tighter causes marked damage, so lower forces become the desired alternative. The radioactivity remaining in the cell pellet gives a good estimation of the "trapped" ECW present.

Measurement of Protein Synthesis

Protein synthesis preferably is measured by determining the rate at which the isolated cells incorporate radioactively labeled amino acid into newly synthesized proteins. This measurement should be taken as soon as possible after the cells are isolated. First, about six stop tubes containing about 2 ml of 10% Trichloracetic acid (TCA) are chilled on ice. Next, a reaction mix is prepared and preincubated to about 37° C. in a shaker incubation bath.

The reaction mix comprises 100 ml q's 0.14M sodium chloride; 25 ml 0.1M tris-hydrochloride, pH 7.5, in 0.14M sodium chloride; 0.50 ml 0.1M magnesium chloride; 0.20 g glucose (dextrose); 0.05 ml MEM with Earl salts and 10 percent fetal bovine serum, such as MEM composition, may be obtained from Gibco, No. 320-1112. To each bottle of MEM is added 15 mg glutamine, 5000 units penicillin, 0.5 mg streptomycin and 10 mg kanamycin.

The reaction mix is filtered using about 0.2 micron pore-size filters. The filtered mix is transferred in aliquots of about ml to 3 ml to sterile polystyrene tubes, capped and irradiated with an ultraviolet light for about 30 minutes. The irradiated mix is frozen. To 200 $\mu$l of this reaction mix, 10 $\mu$l of (4 5)$^3$H-L-leucine containing 1 $\mu$Ci activity is added and preincubated.

About 50 $\mu$l of the diluted cell suspension, prepared as above, is added to each preincubated tube containing the reaction mix and vortexed gently. The time at which the cell suspension is added is noted. The tubes containing the cell suspension are incubated at about 37° C. in a shaker bath. 30 $\mu$l of the cell-containing reaction mix in each tube is removed by pipette from the tube at 10, 20 and 30 minute time periods and transferred to the chilled stop tubes, noting the exact time of each transfer. A blank tube is prepared as a control by adding 24.2 $\mu$l of reaction mix and 5.8 $\mu$l of diluted cell suspension to an empty stop tube, incubating it for 30 minutes and processing it in the same manner as the other six stop tubes. The control tube and the six sample tubes are stored on ice until ready for further processing, but in no event for more than two hours.

The cells from each of the sample-containing stop tubes is filtered. A suitable ten-place filter apparatus with holders, or grids, for 24 mm diameter filters may be obtained from Hoeffer Scientific Instruments (San Francisco, Calif.) Other sizes of filter apparatuses may be obtained from Millipore. A GF/A glass microfibre filter, preferably a 2.4 mm diameter filter (Whatman Co. through Scientific Products Co.), is placed on each of six filter holders on the filter apparatus. The filters are then moistened with a small amount of a wash solution comprising 50 mg 1-leucine per 100 ml of five percent TCA. Vacuum is next applied and each filter is inspected for holes. Faulty filters are replaced, each replacement filter being wetted and inspected.

The sample-containing stop tubes are vigorously vortexed and the sample from each tube is then poured on one of the six filters. The time at which each sample is placed in the stop tube is the stop time of the sample. Each tube is rinsed twice with 2-3 ml of the 5% TCA/-leucine wash solution, 4-5 ml being dispensed to each filter at a time from a squirt bottle. The filters are each given a final wash with 95% ethanol.

The cell-containing filters are allowed to air dry for a few minutes, preferably using vacuum to accelerate drying. Using forceps, each of the dried filters is placed in a scintillation vial and oven dried at about 75° C. for about 30 minutes. The scintillation vials are then removed from the oven and cooled in a desiccator. To each vial 10 ml of scintillation solution, comprising 0.4% PPO and 0.01% POPOP in toluene (w/v), is added.

The uptake of leucine is measured in picomoles (pmoles) of leucine per hour per ml of the original granulocyte suspension. About 10 ml of a leucine solution first is prepared which comprises about 1.0 ml 89 $\mu$M leucine in sterile saline. The final activity of this solution preferably comprises 10 $\mu$l $-$ 1 $\mu$Ci $=$ 1000 pmoles leucine. This solution preferably is kept refrigerated.

The undiluted MEM solution, described above, comprises 52.4 mg leucine per liter. A one percent dilution of this MEM solution would thus provide 400 pmoles of leucine per 100 $\mu$l of diluted MEM. When 100 $\mu$l of the diluted MEM solution is combined with the 10 $\mu$l of the 3H-leucine solution prepared as above, an assay solution comprising a total of 1400 pmoles results.

The DPM's of the assay solution is next determined using a 10 $\mu$l "spot" of a 1:10 dilution of the assay solution on a GF/A filter and the filtration and counting methods and equipment described above for counting incorporation of the isotope by the cells. The counting methods then used to calculate the DPM are preferably those provided in the instruction manual for the counter being used. Often this will be Channels ratio. It should be noted that presently available instruments will provide a filter counting efficiency of about 50 percent.

The preferred isotope, described above, according to the supplier's data comprises 1 $\mu$Ci $=$ 2.22 $\times$ 10$^6$ DPM. Based on this, the sample of 10 $\mu$l then which comprises 0.1 $\mu$Ci should equal about 220,000 DPM's. Dividing this FIGURE into the DPM of the assay calculated as above, usually 50 percent, the efficiency of the counting on filters may be determined. The procedure described above usually yields an efficiency of about 0.7 or 70 percent.

It is believed that the 30 percent loss in efficiency is due to the geometry of the filter in the scintillation vial and is probably not due to quench. For this reason, the use of usual quench correction methods are not preferred. The calculations used to measure leucine uptake should reflect this 30 percent loss of efficiency, such as by dividing the DPM of each sample by 0.7. However, another and preferred method of accounting for the decreased efficiency is to incorporate the correction into each specific activity constant as, for example, by the following equation:

$$\frac{2.22 \times 10^6 \, DPM (\text{in 1 } \mu Ci)}{1400 \text{ pmoles (total leucine in assay)}} = \frac{1586 \, DPM}{\text{pmole}}$$

Then, efficiency loss may be accounted for by multiplying 1586 DPM/pmole by the decimal representing the calculated efficiency. For example, an efficiency of 0.701 would yield 1112 DPM/pmole. The efficiency should be taken for about 10–12 vials to determine an average value for use in the protein synthesis calculation discussed below.

It should be noted that an additional loss of efficiency may be caused by the protein precipitate trapping counts in actual assay procedures. However, as the amount of this additional efficiency loss is believed to be negligible, this fact may be ignored in the above calculations.

The currency of the standard quench curve should be confirmed. This may be done by using the Channels ratio method. Alternatively, if the scintillation equipment being used only has the capacity to measure counts per minute (CPM), the CPM may be measured and divided by the DPM value to give the efficiency. This step may be eliminated if the scintillation counter used prints out all data in the DPM.

At least two CPM measurements are then taken of each cell sample. If the difference between the two values is greater than ten percent, the lower value preferably is used unless a filter leak is suspected. A graph may be prepared showing the cell sample CPM's plotted against elapsed time. In this way, the line should intersect the zero time ordinate between 40 CPM and 100 CPM. The change may be calculated in CPM per hour. The calculated change for duplicate measurements preferably is averaged if the difference is less than ten percent. Inconsistent duplicate measurements of a sample (a difference of greater than ten percent) should be recorded. It should be noted that, in lieu of manual plotting, a linear regression formula may be used.

The equation for calculating protein synthesis by leucine uptake in the cell is as follows:

$$\frac{\frac{CPM/hr - \text{blank}}{\text{counter eff.} \times 0.01} \times \frac{\text{total vol. of assay}}{\text{amt. removed for precipitation}} \times \frac{1,000}{\text{vol. cells used}}}{DPM/\text{pmole leucine}} = \text{pmoles leucine/hr/ml}$$

Measurement of Plasma and Intracellular Amino Acids

Plasma, or extracellular nutrients, and intracellular nutrients include amino acids, electrolytes, minerals, vitamins, glucose products (metabolites), enzymes and other elements required for protein synthesis and energy production to proceed normally. Preferably 19 to 35 amino acids are determined, which, if done according to the procedures described below, will take up to about four hours.

The amino acid level measurements preferably are made with a high pressure single column analyzer. A suitable analyzer is a modified Dionex D-300 Amino Acid/Peptide Analyzer with a Spectro-Physics computing integrator. The automated HPLC system preferably features post column o-phtalaldehyde (OPA) derivatization and fluorescence detection to the picomole level.

A sodium form column (Pickering No. 1193250) preferably is employed in a 25 cm stainless steel tube having an internal diameter of 3 mm. The tube may be packed with a cation exchange resin, such as DC-5A or other similar resin. Amino acids are eluted from the column preferably by sequential application of a series of five specially formulated buffers each at a different pH ranging from 2.2–4.9, at two column temperatures, 46° C. and 69° C. Eluent and reagent pumps preferably are calibrated to deliver reagents at flow rates of about 18 ml per hour.

Plasma (or muscle cell) samples preferably are prepared for analysis by combining 4 parts or 800 $\mu$l of plasma with 1 part or 200 $\mu$l 10 percent sulfosalicylic acid (SSA) to provide final SSA concentration of 2 percent. The mixture is then vortexed and allowed to deproteinate for about 1 hour at about 40° C. The mixture is then centrifuged at about 4000 × g for about 5 minutes and the supernatant collected. A supernatant solution is prepared by combining 11 parts (600 $\mu$l) supernatant with 1 part (54.5 $\mu$l) norleucine (NLEU), internal standard, in 1.0M sodium hydroxide. This plasma (or muscle cell) preparation may be filtered and analyzed, preferably in aliquots of about 40 $\mu$l.

To prepare leukocytes for amino acid analysis, about 400 $\mu$l of the concentrated cell suspension prepared above is frozen to about −20° C. and then thawed to ambient temperature. To the thawed concentrate about 25 $\mu$l of 10 percent SSA is added to provide a final SSA concentration of 0.6%. The mixture is then vortexed and centrifuged in the same manner as the plasma preparation above. The supernatant may then be collected, filtered and analyzed preferably in aliquots of 80 $\mu$l.

A control or standard amino acid solution is also preferably prepared. It may comprise a combination of Pierce No. 20086 and Pierce No. 20087 diluted to a concentration of 25 nm/ml with sodium citrate having a pH of 2.20. The control is analyzed in 40 $\mu$l aliquots.

Each aliquot of plasma, muscle and leukocyte preparation is diluted with a sodium citrate buffer having a pH of 2.20, to have a total volume of 100 $\mu$l. Before the sample for analysis is injected, the column is regenerated with a solution of 0.2N sodium hydroxide and 0.002N EDTA (sodium salt) for ten minutes. An eluent is next injected and reagent pumping is begun. Once the system has reached equilibrium (stable baseline), the diluted aliquot to be analyzed is injected. An initial temperature of 46° C. is used. A first buffer is used to elute phosphoserine, phosphoethanolamine, taurine, methionine sulfoxide, aspartic acid, threonine, serine and aspargine (which are poorly resolved), glutamine, glutamic acid, citrulline, glycine and alanine. At the baseline following alanine, a switch is made to a second buffer in which alpha amino butyric acid and valine are eluted. The temperature of the column is then increased to 69° C. to elute methionine, isoleucine and leucine. Then a third eluent or buffer is introduced to elute phenylalanine, B alanine, amino-isobutyric acid, ethanolamine, gamma-amino butyric acid, ammonia (as ammonium sulfate) and tryptophan. A fourth buffer is next introduced which elutes hydroxylysine, ornithine, 1-methylhistidine, lysine, histidine, 3-methyl-histidine and anserine. A fifth eluent then will be used to elute the remaining amino acids, carnosine and arginine.

During the run, peak areas and retention times are automatically stored by the Spectra-Physics System 1. This information is then printed and preferably is retained for subsequent calculations. Standards preferably are analyzed for control between every four unknowns.

Determination of Primary Nutrients

Once the normal intracellular nutrient levels, such as amino acid levels, for the selected population and the normal rate of protein synthesis has been identified, it may then be determined which subset of the intracellular nutrients normally are primary for protein synthesis or other selected metabolic process; that is, which subgroup of, for example, the amino acids have the most substantial impact on the cell's ability to synthesize protein. Standard or normal primary nutrients may be determined by application of a multivariate statistical analysis preferably carried out by computer on a population of analogous study subjects.

As used herein the term "analogous subjects" refers to study subjects having similar relevant characteristics to the subject in need of treatment. For example, in most cases study subjects will be selected according to age group. Other factors also may be relevant.

It is believed that subsets of certain primary nutrients (and secondary nutrients) will be found to be standards for a selected population. However, what are normal primary nutrients will vary according to the age, sex or physical condition of the subjects in the selected population.

Determination of Secondary Nutrients

Next it is determined which plasma nutrients in the study subjects normally best predicted changes in the level of each of the primary nutrients, thereby having a secondary or indirect effect on the level of primary nutrients. Such secondary nutrients may be identified also by use of a multivariate statistical analysis procedure, also preferably performed by computer. This analysis produces for each secondary amino acid or nutrient a partial regression coefficient which is expressed as a decimal number having a positive or negative sign.

Evaluation of Subject in Need of Therapy

In accordance with the present invention, the nutritional status of a subject believed to be in need of therapy first is assessed. This is done by measuring the rate of one or more selected intracellular metabolic processes. Most preferably the rate of protein synthesis will be measured as described above. However, it often will be useful also to measure glucose metabolism or energy production or both.

For each of the subject's metabolic processes which is found to be abnormal, a set of primary intracellular nutrients is identified based on the normal set found in an analogous study population. The subject's intracellular level of each of the primary nutrients next is measured. Then, those which are present at abnormal levels are identified based on the normal levels identified for the study population.

Preparation of the Nutrient Composition

Having identified the subject's abnormal primary nutrients for the selected malfunctioning metabolic process, a nutrient composition is prepared for treating the disorder. First, the set of secondary nutrients for each of the subject's abnormal primary nutrients is identified by reference to normal sets found in an analogous study population.

The nutrient composition comprises an adjusted concentration of each of the secondary extracellular nutrients for each of the subject's abnormal primary nutrients. By way of example, assume the subject to be treated is an adult with an abnormally low protein synthesis rate.

As shown in the examples below, in an analogous study population one of the primary nutrients for protein synthesis is leucine. Multivariate statistical analysis determined that the secondary extracellular nutrients for leucine are threonine, citrulline, valine and histidine, having partial regression coefficients of $+0.12$, $-0.27$, $-0.06$, and $-0.39$, respectively. (See Table A below.)

First, the coefficients, disregarding sign and expressed as whole numbers, are totaled. In this case the sum of the coefficients, disregarding sign, for threonine (12), citrulline (27), valine (6) and histidine (39) is 84. Next, the percentage of this sum represented by each secondary nutrient is computed and may be rounded off to the nearest whole number. In the present example, the percentages are $+14\%$ for threonine, $-32\%$ for citrulline, $-7\%$ for valine and $-46\%$, respectively.

The extent to which the treatment concentration varies from normal is determined by the percentage of that secondary amino acid's coefficient in the coefficient total. The concentrations of the secondary nutrients in the nutrient composition are adjusted to be above normal, where the coefficient is a positive number, and below normal, where the coefficient is a negative number.

Thus, the nutrient composition for the subject in this example, which requires normalization of the intracellular level of leucine should contain a threonine concentration about 14% higher (because threonine's coefficient has a positive sign) than the threonine concentration found to be normal in the study population. Similarly, the nutrient composition should contain a citrulline concentration 32% lower than normal for citrulline, a valine concentration 7% lower than the normal valine level and a histidine concentration 39% lower than the normal histidine level (because the coefficient for each of these amino acids had a negative sign).

Preferably, the nutrient composition also would comprise other nutrients, including the deficient primary nutrients, if any, at their normal extracellular concentrations. In this way, all nutrients are available for proper metabolic functioning.

Now it will be understood that the nutrient concentration comprises the identified secondary nutrients in non-normal concentrations, i.e., adjusted to above or below the normal extracellular concentration to produce relative concentrations based on the proportional statistical significance of each of those secondary nutrients to the subject's abnormal primary nutrient. For ease of computation the concentration of each of the secondary nutrients in the nutrient composition may be calculated according to the following formula:

$$[F] = A[B] + [B]$$

where "[F]" is the final "adjusted" concentration in nanomoles per milliliter of the secondary nutrient; where "A" equals the partial regression coefficient of the secondary nutrient, including sign, divided by the sum of the coefficients, disregarding their signs, of all the secondary nutrients, such sum being expressed as a positive number; and where "[B]" is the normal extracellular concentration of the secondary nutrient in the study population expressed in nanomoles per milliliter. It will be appreciated that the same result obtains when the coefficients are expressed as whole numbers.

Verification of Efficacy of Proposed Therapy

Prior to treating the subject, it is preferred to verify that administration of a nutrient composition comprising the secondary nutrients will be effective in vivo to treat the subject's nutritional disorder; that is, to result in improved function of the metabolic processes, such as protein synthesis. In vitro testing is a preferred verification method.

A nutrient composition is prepared comprising the subject's pre-determined secondary nutrients selected in response to the subject's intracellular primary nutrient levels and determined as described above, in concentrations effective to improve metabolic function as previously described.

A fresh venous blood sample is obtained from the subject using the same procedure as described above. The cells, such as granulocytes, are isolated and prepared as before and incubated in the nutrient composition at 37° C. for about thirty minutes. After incubation, the rate of protein synthesis in the subject's leukocytes is measured, also as described above. If the incubated granulocytes demonstrate improved in vitro protein synthesis, as predicted, the efficacy of treating the subject with the proposed nutrient composition is verified.

Administration of Nutrient Composition

The nutrient composition is administered to the subject in an amount effective to treat the disorder. The composition may be administered intravenously or enterally. The effective amount preferably is determined by reference to parameters such as the subject's body weight and surface area, and other relevant variables including the extent of the subject's disorder. Typically, nutrient compositions comprising amino acid solutions range from about 3% to about 10%, with a preferred range of about 5%. The rate of infusion preferably is adjusted so that preferably from about 0.5 grams to about 1.5 grams of amino acids per kilogram of body-weight per day are given.

At intervals during and following administration of the nutrient composition, it is preferable to monitor the effect of the therapy on the subject by periodic assessment of improvement of metabolic function, such as by measuring the rate of protein synthesis. Further, periodic reassessment of the subject's intracellular and plasma nutrient levels may lead to modifications of the prescribed nutrient composition to promote enhancement of protein synthesis or other nutrient-dependent intracellular processes.

It is to be understood that measurement of other parameters of metabolic function may be useful in assessing nutritional status. These parameters include, but are not limited to, intracellular energy charge, glycolytic enzyme activity, adenine nucleotide activity, DNA values and protein levels.

EXAMPLES

Comparison of Intracellular and Plasma Levels of Amino Acids

A study was conducted in which venous blood samples were obtained from each of 29 normal adults. Each sample was obtained, prepared and tested substantially as described above. The concentrations were expressed in nanomoles per milliliter of intracellular water. The intracellular concentrations of amino acids were compared to the concurrent plasma levels of the same amino acids. The concentrations of aspartic acid, glutamine, glutamic acid, serine, asparagine and glycine varied substantially, the differences ranging from about 400 nm/ml ICW (aspartic acid) to about 1300 nm/ml ICW (glutamine, serine and asparagine). The difference between intracellular and extracellular amino acids was at least significant in all but two amino acids, namely valine and citrulline.

A similar study was performed using 57 normal infants. In this study, the differences for arginine, glutamic acid, glycine and tyrosine ranged from about 700 nm/ml ICW to about 2000 nm/ml ICW. The difference was statistically significant for all the amino acids except for phenylalanine, tyrosine and valine. Although the intracellular-plasma variance occurred to a different extent and was substantial in different amino acids in the infant than in adults, it is demonstrated that plasma levels of amino acids do not accurately reflect intracellular levels of the same amino acids. It is suggested that measurement of intracellular amino acids is required to accurately assess the amino acid substrate available at the cellular level for nutrient-dependent processes, such as protein synthesis.

2. Comparison of Rate at Which Intracellular Amino Acids and Plasma Amino Acids Respond to Therapy The intracellular and plasma levels of 18 amino acids in 13 uremic adults were measured for a baseline at a visit to the dialysis center. These values were expressed as percentages of a control value for each amino acid. The plasma levels of 9 of the 18 amino acids were equal to or less than 100% of the control plasma value. The intracellular levels of 8 amino acids equaled or exceeded 100% of the control.

The same uremic adults were tested again after about two months of dialysis treatment. A dramatic change in intracellular amino acid composition was demonstrated. The concentrations of some of the amino acids increased and some decreased. However, after about two months of treatment, the intracellular level of all but two, or a total of 16, of the amino acids equaled or exceeded 100% of control. One of the two amino acids which were measured at less than 100% of control had at least increased since the first visit.

On the other hand, the plasma levels of amino acids in these uremic adults did not so dramatically reflect the effect of therapy. At the time of the second visit, only seven of the 18 amino acids equaled or exceeded 100% of control.

Based upon these results, it is concluded that there is no relation between intracellular and plasma levels. The extracellular amino acid levels usually are not corrected with the intracellular levels. The amino acid concentrations in the plasma are a function of amino acids entering the plasma from various organs, such as the liver and muscle, and movement of other amino acids from the plasma into various organs, such as the liver or muscle. Thus, intracellular amino acid imbalance is a better indicator of nutritional status than corresponding extracellular imbalance.

In contrast, in another study 11 uremic subjects being treated by hemodialysis received a standard amino acid solution by infusion three times per week following each of their dialytic sessions. Protein synthesis, intracellular and plasma amino acids were measured as a baseline. The primary intracellular amino acids predicting the abnormally low level of protein synthesis in these uremics were aspartic, glutamate, glycine, ornithine and arginine. Compared to controls, the intracellular levels of aspartate, glycine, and arginine were significantly increased, while ornithine was decreased.

Following three months of infusions of a standard commercial amino acid solution, i.e., a solution which was not specifically designed to correct the abnormal levels of the primary nutrients as described herein, the abnormal levels of the primary amino acids were not corrected. The array of primary intracellular amino acid predictors of protein synthesis had changed and included aspartate, valine, isoleucine, ornithine, lysine and tryptophan. However, the concentrations of all of these amino acids remained abnormal and decreased from 25% to 76% of their baseline values. Protein synthesis was not improved.

This study shows that administration of a standard commercially available and commonly used intravenous amino acid mixture, not specifically designed to correct abnormal levels of primary (intracellular) amino acids, does not selectively improve abnormalities in the concentrations of primary intracellular amino acids associated with protein synthesis. Nor in these uremic patients does it improve protein synthesis.

3. Effect of Adjusted Amino Acid Levels on Protein Synthesis

The rate of protein synthesis occurring in leukocytes of uremic patients after a few stabilizing dialysis treatments was compared to their protein synthesis rate after about three months of dialysis therapy. A marked increase was demonstrated. From this, it was concluded that adjustment towards normal of intracellular amino acids was associated with increased protein synthesis and thus, an improved nutritional status.

4. Determination of Primary Amino Acids

Protein synthesis and intracellular levels of 17 amino acids were measured in 29 normal adults. A multivariate statistical analysis was made by computer of the results. Based on the measured protein synthesis rate of 2585 pmoles/hr/mgDNA, a subset of intracellular amino acids was identified which best predicted ($R^2=0.54$) protein synthesis. The subset comprised methionine, isoleucine, leucine, phenylalanine and histidine. These amino acids had partial regression coefficients of $-154$, $+295$, $-80$ and $+147$, respectively.

Similarly, a subset of six primary intracellular amino acids was identified for 54 neonates. The mean rate of protein synthesis was 4043 pmoles/hr/mgDNA. The subset comprised leucine, methionine, tyrosine, glycine, alanine and taurine. The coefficients for each of these amino acids were $+84.1$, $-222.4$, $-39.2$, $+9.5$, $-33.0$ and $-0.5$, respectively. This subset accounted for a variance in protein synthesis ($R^2$) equal to 0.365 ($p=0.001$).

5. Determination of Secondary Amino Acids

A multivariate analysis of the 29 normal adults tested in Example Nos. 1 and 4 above demonstrated that the intracellular level of each of the primary amino acids was predominately related to a distinct subset of secondary amino acids in the plasma. The results are shown in Table A.

TABLE A

Relationship and Effect of Statistically Selected Secondary (Plasma) Amino Acids on Statistically Selected Primary (Intracellular) Amino Acids (A.A.) in 29 Normal Adults

| Primary A.A. | Secondary A.A. | $R^2$ | p |
|---|---|---|---|
| Isoleucine$_{IC}$ = | 11.6 $-0.09$* (citrulline) $+0.09$ (isoleucine) $-0.09$ (histidine) | 0.61 | 0.0001 |
| Leucine$_{IC}$ = | 29.1 $+0.12$ (threonine) $-0.27$ (citrulline) $-0.06$ (valine) $-0.39$ (histidine) | 0.60 | 0.0001 |
| Methionine$_{IC}$ = | 4.6 $+0.03$ (taurine) $-0.07$ (citrulline) | 0.19 | 0.060 |
| Phenylalanine$_{IC}$ = | 6.3 $+0.72$ (aspartic acid) $-0.05$ (citrulline) $+0.32$ (methionine) $+0.06$ (tyrosine) $-0.19$ (histidine) | 0.69 | 0.0001 |
| Histidine$_{IC}$ = | 6.3 $-0.04$ (citrulline) $-0.02$ (valine) $-0.08$ (leucine) $-0.08$ (phenylalanine) $-0.08$ (ornithine) $+0.05$ (arginine) | 0.75 | 0.0001 |

*Partial Regression Coefficients

A multivariate analysis of the six intracellular primary amino acids and the plasma levels of amino acids as studied in 54 normal neonates demonstrated the results shown in Table B.

TABLE B

Relationship and Effect of Statistically Selected Secondary (Plasma) Amino Acids on Statistically Selected Primary (Intracellular) Amino Acids (A.A.) in 54 Normal Neonates

| Primary A.A. | Secondary A.A. | $R^2$ | p |
|---|---|---|---|
| Leucine | 0.5* (methionine) $-0.02$ (phenylalanine) $-0.02$ (arginine) $-0.7$ (citrulline) $+0.02$ (ornithine) $+0.2$ (taurine) | 0.49 | 0.0001 |
| Methionine | $-0.08$ (tryptophan) $+0.01$ (histidine) $-0.06$ (arginine) $-0.03$ (glutamic) $-0.09$ (citrulline) $+0.06$ (taurine) | 0.44 | 0.0002 |
| Tyrosine | 0.08 (isoleucine) $+0.03$ (lysine) $+0.1$ (histidine) $-0.1$ (arginine) $-0.05$ (glutamic) $-0.2$ (citrulline) | 0.45 | 0.0001 |
| Taurine | 10.3 (isoleucine) $+13.3$ (lysine) $-18.6$ (histidine) $-8.1$ (arginine) $-39.6$ (aspartic acid) $+2.6$ (glycine) | 0.45 | 0.0001 |
| Glycine | $-1.9$ (valine) $+4.3$ (methionine) $+2.7$ (lysine) $-4.0$ (histidine) $+1.0$ (tyrosine) $+1.9$ (taurine) | 0.39 | 0.001 |
| Alanine | 1.0 (methionine) $-1.1$ (phenylalanine) $+0.3$ (lysine) $+0.2$ (glutamic) $-1.6$ (citrulline) $+0.5$ (taurine) | 0.38 | 0.001 |

*Partial Regression Coefficients

Based on the data in Tables A and B, it was concluded that a subject having an abnormal level of a selected primary nutrient may be successfully treated by administration of a nutrient solution comprising the nutrients identified as secondary to the abnormal primary nutrient. Adjustment of the subject's secondary nutrients could either increase or decrease the abnormal level of the primary nutrient, as needed. This restores the balance within the set of primary nutrients.

Based on the foregoing, it is apparent that the method of the present invention makes possible treatment of nutritional disorders by administration of a nutrient composition comprising those nutrients specifically required for improved metabolic function and at specific concentrations. Such therapy minimizes exposure of the subject to unneeded exogenous and potentially detrimental substances and also minimizes expense of nutritional therapy.

Changes may be made in the nature, composition, operation and arrangement of the various elements, steps and procedures described herein without departing from the spirit and scope of the invention as defined in the following claims.

What is claimed:

1. A method for treating a subject for a nutritional disorder, comprising:

measuring in the subject the rate of a selected intracellular metabolic process;

for the selected intracellular metabolic process, identifying a set of primary nutrients based on a multivariate statistical analysis of a population of normal study subjects analogous to the subject to be treated;

measuring each of the subject's primary nutrients and determining which is present at an abnormal level based on normal levels identified for the study population;

for each of the subject's primary nutrients which is present at an abnormal level, identifying a set of secondary nutrients based on the normal set of secondary nutrients in the study population determined by applying multivariate statistical analysis for each of the primary nutrients in the study population and producing for each secondary nutrient a partial regression coefficient having a positive or negative sign; and administering to the subject an effective amount of a nutrient composition comprising each of the identified secondary nutrients, wherein the amount of each secondary nutrient is determined according to the following formula:

$$[F] = A[B] + [B]$$

where "[F]" is the final concentration in nanomoles per milliliter of the secondary nutrient in the nutrient composition; where "A" equals the partial regression coefficient of the secondary nutrient divided by the sum of the coefficients of all the secondary nutrients, disregarding their signs, such sum being expressed as a positive number; and where "[B]" is the normal extracellular concentration of the secondary nutrient in the study population expressed in nanomoles per milliliter.

2. The method of claim 1 wherein the nutrient composition further comprises the primary nutrient present intracellularly at abnormal levels.

3. The method of claim 1 wherein the selected metabolic process is protein synthesis.

4. The method of claim 1 wherein energy production is the selected intracellular metabolic process.

5. The method claim 1 in which glucose metabolism is the selected intracellular metabolic process.

6. The method claim 1 in which the primary nutrient determined to be present at an abnormal level is an amino acid.

7. The method claim 1 in which the secondary nutrients are amino acids.

* * * * *

UNITED STATES PATENT AND TRADEMARK OFFICE
CERTIFICATE OF CORRECTION

PATENT NO. : 5,051,249
DATED : September 24, 1991
INVENTOR(S) : Jack Metcoff

It is certified that error appears in the above—identified patent and that said Letters Patent is hereby corrected as shown below:

Col. 4, line 58, please delete the numeral "10".

Col. 7, line 38, please insert the numeral -- 2 -- after the word "about".

Col. 8, line 52, please delete the word "FIGURE" and substitute therefor the word -- figure --.

Col. 13, line 59, at the margin please insert the numeral -- 1. --.

UNITED STATES PATENT AND TRADEMARK OFFICE
CERTIFICATE OF CORRECTION

PATENT NO. : 5,051,249

DATED : September 24, 1991

INVENTOR(S) : Jack Metcoff

It is certified that error appears in the above-identified patent and that said Letters Patent is hereby corrected as shown below:

Col. 16, line 57, please delete the word "an" and substitute therefor the word -- a --.

Signed and Sealed this

Ninth Day of February, 1993

*Attest:*

STEPHEN G. KUNIN

*Attesting Officer*     *Acting Commissioner of Patents and Trademarks*